United States Patent [19]

Lachnit-Fixson

[11] 3,969,502
[45] *July 13, 1976

[54] METHOD FOR CONTRACEPTION BY THE ADMINISTRATION OF SEQUENTIAL CONTRACEPTIVE PREPARATIONS

[75] Inventor: Ursula Lachnit-Fixson, Berlin, Germany

[73] Assignee: Schering Aktiengesellschaft, Berin & Bergkamen, Germany

[ * ] Notice: The portion of the term of this patent subsequent to Feb. 17, 1993, has been disclaimed.

[22] Filed: July 9, 1974

[21] Appl. No.: 486,757

Related U.S. Application Data

[63] Continuation-in-part of Ser. No. 350,590, April 12, 1973, Pat. No. 3,939,264.

[30] Foreign Application Priority Data

Apr. 14, 1972  Germany............................ 2218831
Mar. 3, 1973  Germany............................ 2310963
July 9, 1973  Germany............................ 2335265

[52] U.S. Cl................................ 424/239; 424/241
[51] Int. Cl.²......................................... A61K 31/56
[58] Field of Search............................ 424/239, 241

[56]  References Cited
UNITED STATES PATENTS 3,409,721  11/1968  Applezweig.......................... 424/241
3,568,828  3/1971  Lerner................................ 424/239

*Primary Examiner*—Elbert L. Roberts
*Attorney, Agent, or Firm*—Millen, Raptes & White

[57]  ABSTRACT

Method of contraception over a 21-day cycle in which an estrogen and a progestogen are administered in a low dosage for 10–12 days and thereafter at a slightly higher dosage for the next 11–9 days.

9 Claims, No Drawings

METHOD FOR CONTRACEPTION BY THE ADMINISTRATION OF SEQUENTIAL CONTRACEPTIVE PREPARATIONS

BACKGROUND OF THE INVENTION

This is a continuation-in-part of application Ser. No. 350,590, filed Apr. 12, 1973, now U.S. Pat. No. 3,939,264.

Numerous hormonal methods for contraception are known, i.e.., the oral administration of combination-type preparations, e.g., "Ovulen," "Anovlar," "Lyndiol," and similar combinations of estrogenic and gestagenic active agents. Also conventional is the administration of purely sequential preparations such as, for example, "Ovanone," etc., wherein first an estrogen is administered at a high dosage in the absence of gestagen, over a period of 7 days, and thereafter the estrogen is administered at the same high dosage in combination with a relatively high amount of gestagen over a period of 15 days, with the next 6 days being a blank period without administration of estrogenic or gestagenic agent in order to mimic the normal 28-day menstrual cycle of the woman.

The administration of modified sequential preparations is likewise conventional, such as, for example, "Kombiquens," "Tri-Ervonum," and "Oraconal," etc., wherein first an estrogen is administered at a high dosage in combination with a low amount of gestagen over a period of 16 days, and subsequently the estrogen is administered over a period of about 7 days at the same high dosage in combination with an amount of gestagen about 5–10 times the original amount. See U.S. Pat. No. 3,568,828. To adapt to the natural 28-day cycle of the female, a 5-day hormone-free period follows the administration of these preparations wherein placebos or any desired other non-contraceptive effective agents are taken, such as, for example, tonics, iron supplements, etc.

The disadvantages of the administration of the above-mentioned sequential preparations are, in particular, the relatively high doses of estrogen, resulting, in addition to evoking the customary symptoms caused by an excess of estrogen, such as, for example, gastrointestinal disturbances, nausea, weight gain from edema, etc., along with an increase in the risk of thromboembolism. On the other hand, however, it was considered essential to ingest high doses of estrogen for reliable contraceptive effect.

SUMMARY OF THE INVENTION

According to this invention, reliable contraception is achieved by first administering as a first stage a combination of an estrogen and a progestogen both at a lower but contraceptively effective daily dosage over a period of 10–12 days and then for the next 11–9 days, administering as a second stage a slightly higher daily dose, up to two times that of the first stage, and a progestogen at a slightly higher daily dosage up to three times that of the first stage. Thereafter, to adapt to the normal female cycle of about 28 days, no estrogens and progestogens are administered for the following 5–7 days, for a total of about 28 days. This latter phase can be without medication of any drug in a conventional manner, placebos or a non-contraceptive active effective agent can be administered without adversely affecting the method.

In its composition aspect, this invention relates to a two-stage oral contraceptive composition consisting essentially of about 21–23 separate dosage units adapted for successive daily oral ingestion of which the first 10–12 dosage units contain in admixture with a pharmaceutically acceptable carrier an estrogen and a progestogen at lower respective dosages, and the next 11–9 dosage units can contain in admixture with a pharmaceutically acceptable carrier an estrogen and a progestogen at higher respective dosages, and any remaining units being free of estrogenic and progestogenic agents.

DETAILED DISCUSSION

By the method of this invention, it is possible to administer lower doses of estrogen by the sequential method, which is strongly recommended to physicians, wherein the reduced estrogen dose in the first application phase still further decreases the estrogen burden. Also, by increasing the amount of progestogen in the middle of the administration phase, the occurrence of the normal cycle, i.e., the normal physiological processes, is initiated. By this quasi-adaptation to the physiological cycle, the preparations are more compatible and improved metabolic parameters result. Furthermore, an optimum control is exerted on the menstrual cycle.

The term "lower dosage" as used herein means a dose lower, e.g., 60 to 20 %, preferably 50 to 30 %, of the contraceptive dose conventional for the selected effective estrogen.

The term "higher dosage" as used herein means a dose higher than that employed in the first stage, up to two times in the case of the estrogen and up to three times in the case of the progestogen. Usually this dosage will be 50 to 100 % of the contraceptive dose conventional for the selected effective agent.

Suitable as the estrogen component for the method of this invention are the conventional estrogens. In this connection, the estrogen employed should preferably be administered in such doses that the amount of estrogen utilized according to the invention in the first 10–12 days is equal to that corresponding to the administration of 0.025 – 0.035 mg. daily of 17α-ethinylestradiol. The amount of estrogen utilized according to this invention in the 11–9 days of the second phase is to be equal to that corresponding to the administration of about 0.030 – 0.050 mg. daily of 17α-ethinylestradiol. Inter alia, suitable estrogen components are also the 17α-ethinylestradiol esters or ethers. Furthermore, the natural estrogens can be used, e.g., estrone, estradiol or estriol, and the esters thereof, inter alis estradiol valerate. 17α-Ethinylestradiol and estradiol valerate are preferred.

All progestationally active substances are suitable for use as the progestogen component according to the present invention. In this connection, the progestogen employed should be applied in such dosages that the amount of progestogen utilized according to the invention in the first 10–12 days is equal to that corresponding to the administration of 0.050 – 0.125 mg. daily of d-norgestrel. The quantity of progestogen used according to the invention in the 11–9 days of the second phase is to be equal to that corresponding to the administration of about 0.100 – 0.350 mg. daily of d-norgestrel.

Suitable as the progestrogen component, inter alia, are progesterone or the derivatives thereof, e.g., 17- hydroxyprogester-one esters and 19-nor-17-hydroxyprogesterone esters, 17α-ethinyltestosterone, as well as 17α-ethinyl-19-nortestosterone, and the derivatives thereof. Derivatives are understood to mean compounds formed with the introduction of a double bond or double bonds, by substitution, or by the production of functional derivatives, such as, for example, esters, ethers, ketals, etc.

The double bonds can be present, inter alia, in the 1(2)-, 6(7)-, and/or 16(17)-positions. Suitable substituents are, inter alia, halogen, especially fluorine, chlorine, and bromine atoms, lower alkyl, especially the methyl group, alkenyl, alkinyl, particularly the ethinyl group, and/or the hydroxy group, which can be in the 4-, 6-, 7-, 16- and/or 17-positions, as well as methylene groups which can be in the 1(2)-, 6(7)-, 15(16)- and/or 16(17)-positions. Suitable esters are the esters of the acids usually employed in the steroid chemistry for the esterification of the steroid alcohols. Examples are alkanecarboxylic acids, particularly alkanecarboxylic acids of 1–7 carbon atoms. Examples for ethers are alkyl and tetrahydropyranyl ethers. Suitable ketals are, for example, those of ethanediol or those of the propanediols.

Preferred progestogens are d-norgestrel, 17α-ethinyl-19-nortestosterone acetate, and cyproterone acetate.

The progestogen (or estrogen, respectively) contained according to the invention in the combination with the estrogen (or progestogen, respectively) can be the same or also a different one in the first and second stages. If different progestogens (or estrogens) are used in the first and second stages, the present method, in addition to the aforedescribed advantages, has the further advantage of reducing or eliminating the side effects of a certain progestogen (or estrogen), in that this progestogen (or estrogen) is administered merely in one stage, while in the other stage a different progestogen (or estrogen) having a competitive array of side effects is administered.

Thus, it is possible, for example, to utilize in one stage the estrogen in combination with a progestogen derived from testosterone or 19-nortestosterone and having, in the 17α-position, optionally a substituted hydrocarbon residue. These (19-nor)-testosterone derivatives generally exhibit a low androgenic side effect. In the other stage, the estrogen can then be employed in combination with a progestogen derived from progesterone and which does not have the androgenic side effect inherent in the testosterone or 19-nortestosterone compounds. Progesterone derivatives having an antiandrogenic side effect in addition to the progestational effect are considered particularly advantageous progestogens.

It is also possible, for example, to utilize, in one stage, the progestogen in combination with an estrogen derived from 17α-ethinylestradiol. These compounds generally have a lesser gastric compatibility and a stronger effect on the carbohydrate and fat metabolism. In the other stage, the progestogen can then be used in combination with an estrogen derived from the natural estrogen and which does not have the above-described side effects.

If different progestogens are utilized in the first and second stages, a preferred embodiment is to utilize, in the first stage, the estrogen in combination with a testosterone or 19-nortestosterone derivative and, in the second stage, the estrogen in combination with a progesterone derivative.

If different estrogens are used in the first and second stages, preferred embodiment is to utilize, in the first stage, the progestogen in combination with a 17α-ethinylestradiol derivative and, in the second stage, the progestogen in combination with an estrogen which does not contain a 17α-ethinyl group.

The estrogenic and progestational effective agent components are preferably administered orally, but they can also be applied separately or parenterally. For this purpose, the effective agents are processed, together with the additives, vehicles and/or flavor-ameliorating substances, into the usual forms of application in accordance with methods known per se. For the preferred oral administration, especially suitable are tablets, dragees, capsules, pills, suspensions, or solutions, and for parenteral application, in particular, oily solutions, such as, for example, sesame oil or castor oil solutions which can optionally contain additionally a diluent, such as, e.g., benzyl benzoate or benzyl alcohol.

The oral contraceptive compositions adapted for oral ingestion are provided as a packaged sequence of unit dosage forms adapted for oral ingestion of one unit dosage form daily in sequence for 19–23 days, preferably 21 days, preferably followed in sequence by about 5–7 placebos to provide a total of 28 unit dosages per package. The unit dosages are preferably packaged in the conventional bubble plastic package having 28 bubbles in a sheet of flexible plastic arranged in a oval or circle, each containing a unit dosage with the placebos being positioned so as to be ingested last. The bubbles are sealed by a tangible sheet which is adapted to break and release the unit dosage when the bubble is pressed.

Without further elaboration, it is believed that one skilled in the art can, using the preceding description, utilize the present invention to its fullest extent. The following specific embodiments are, therefore, to be construed as merely illustrative, and not limitative of the remainder of the disclosure in any way whatsoever.

EXAMPLE 1

(Composition of a Dragee, per Stage)

| | | |
|---|---|---|
| First Stage: | 0.030 mg. | 17α-Ethinylestradiol |
| | 0.050 mg. | d-Norgestrel |
| | 33.170 mg. | Lactose |
| | 18.000 mg. | Corn starch |
| | 2.100 mg. | Polyvinylpyrrolidone |
| | 1.650 mg. | Talc |
| | 55.000 mg. | Total weight, which is supplemented to about 90 mg. with the usual sugar mixture. |
| Second Stage: | 0.040 mg. | 17α-Ethinylestradiol |
| | 0.125 mg. | d-Norgestrel |
| | 33.085 mg. | Lactose |
| | 18.000 mg. | Corn starch |
| | 2.100 mg. | Polyvinylpyrrolidone |
| | 1.650 mg. | Talc |
| | 55.000 mg. | Total weight, which is supplemented to about 90 mg. with the usual sugar mixture. |

EXAMPLE 2

(Composition of a Tablet, per Stage)

| | | |
|---|---|---|
| First Stage: | 0.030 mg. | 17α-Ethinylestradiol |
| | 1.000 mg. | 17α-Ethinyl-19-nortestosterone acetate |
| | 32.120 mg. | Lactose |

EXAMPLE 2-continued

(Composition of a Tablet, per Stage)

|  |  |  |
|---|---|---|
|  | 18.000 mg. | Corn starch |
|  | 2.100 mg. | Polyvinylpyrrolidone |
|  | 1.650 mg. | Talc |
|  | 0.100 mg. | Magnesium stearate |
|  | 55.000 mg. | Total weight, which is supplemented to about 90 mg. with the usual sugar mixture. |
| Second Stage: | 0.050 mg. | 17α-Ethinylestradiol |
|  | 2.000 mg. | 17α-Ethinyl-19-nortestosterone acetate |
|  | 31.100 mg. | Lactose |
|  | 18.000 mg. | Corn starch |
|  | 2.100 mg. | Polyvinylpyrrolidone |
|  | 1.650 mg. | Talc |
|  | 0.100 mg. | Magnesium stearate |
|  | 55.000 mg. | Total weight, supplemented to about 90 mg. with the usual sugar mixture. |

EXAMPLE 3

(Composition of a Tablet, per Stage)

|  |  |  |
|---|---|---|
| First Stage: | 0.030 mg. | 17α-Ethinylestradiol |
|  | 1.000 mg. | 17α-Ethinyl-19-nortestosterone acetate |
|  | 32.120 mg. | Lactose |
|  | 18.000 mg. | Corn starch |
|  | 2.100 mg. | Polyvinylpyrrolidone |
|  | 1.650 mg. | Talc |
|  | 0.100 mg. | Magnesium stearate |
|  | 55.000 mg. | Total weight, which is supplemented to about 90 mg. with the usual sugar mixture. |
| Second Stage: | 0.050 mg. | 17α-Ethinylestradiol |
|  | 2.000 mg. | Cyproterone acetate |
|  | 31.100 mg. | Lactose |
|  | 18.000 mg. | Corn starch |
|  | 2.100 mg. | Polyvinylpyrrolidone |
|  | 1.650 mg. | Talc |
|  | 0.100 mg. | Magnesium stearate |
|  | 55.000 mg. | Total weight, which is supplemented to about 90 mg. with the usual sugar mixture. |

EXAMPLE 4

(Composition of a Dragee, per Stage)

|  |  |  |
|---|---|---|
| First Stage: | 1.800 mg. | Estradiol valerate |
|  | 0.100 mg. | d-Norgestrel |
|  | 31.350 mg. | Lactose |
|  | 18.000 mg. | Corn starch |
|  | 2.100 mg. | Polyvinylpyrrolidone |
|  | 1.650 mg. | Talc |
|  | 55.000 mg. | Total weight, which is supplemented with the usual sugar mixture to about 90 mg. |
| Second Stage: | 2.400 mg. | Estradiol valerate |
|  | 0.120 mg. | 17-Acetoxy-18-methyl-15α,16α-methylene-19-nor-4-pregnene-3,20-dione |
|  | 30.780 mg. | Lactose |
|  | 18.000 mg. | Corn starch |
|  | 2.100 mg. | Polyvinylpyrrolidone |
|  | 1.600 mg. | Talc |
|  | 55.000 mg. | Total weight, which is supplemented with the usual sugar mixture to about 90 mg. |

EXAMPLE 5

(Composition of a Dragee, per Stage)

|  |  |  |
|---|---|---|
| First Stage: | 1.800 mg. | Estradiol valerate |
|  | 0.100 mg. | d-Norgestrel |
|  | 31.350 mg. | Lactose |
|  | 18.000 mg. | Corn starch |
|  | 2.100 mg. | Polyvinylpyrrolidone |
|  | 1.650 mg. | Talc |
|  | 55.000 mg. | Total weight, which is supplemented with the usual sugar mixture to about 90 mg. |
| Second Stage: | 2.000 mg. | Estradiol valerate |
|  | 0.150 mg. | d-Norgestrel |
|  | 31.100 mg. | Lactose |
|  | 18.000 mg. | Corn starch |
|  | 2.100 mg. | Polyvinylpyrrolidone |
|  | 1.650 mg. | Talc |
|  | 55.000 mg. | Total weight, which is supplemented with the usual sugar mixture to 90 mg. |

CLINICAL TESTS

EXAMPLE 6

The first stage of preparation according to Example 5 was administered to each of five women of child-bearing age daily for 11 days (first stage) and the second stage thereof was administered daily for the following 10 days (second stage). The subsequent 7 days, during which the menstrual bleeding occurred, were without administration.

During the entire treatment period, the cycles were anovulatory. The preparation was of excellent compatibility; the number of intermediate and spot bleeding was considerably reduced as compared to these occurrences prior to treatment; the side effects were likewise, in part, markedly reduced as compared to the last cycle prior to treatment.

What is claimed is:

1. A method of contraception wherein a combination of an estrogen and a progestogen is administered orally to a female of child-bearing age for about 21 days and for the next 5–7 days, for a total of about 28 days, no estrogens and progestogens are administered, which comprises administering orally daily for the first 10–12 days either a combination of:

a. 0.030 mg. of 17α-ethinylestradiol and
   0.050 mg. of d-norgestrel, or a combination of:

b. 0.030 mg. of 17α-ethinylestradiol and
   1 mg. of 17α-ethinyl-19-nortestosterone acetate;

and then administering orally daily for the next 11–9 days, when combination (a) is administered for the first 10–12 days, a combination of c. 0.040 mg. of 17α-ethinylestradiol and
   0.125 mg. of d-norgestrel, or when combination (b) is administered for the first 10–12 days, a combination either of:

d. 0.050 mg. of 17α-ethinylestradiol and
   2 mg. of 17-ethinyl-19-nortestosterone acetate; or e. 0.050 mg. of 17-ethinylestradiol and
   2 mg. of cyproterone acetate.

2. A method according to claim 1 wherein for the first 10–12 days 0.030 mg. of 17α-ethinylestradiol and 0.050 mg. of d-norgestrel are administered daily and for the next 11–9 days 0.040 days 0.040 mg. of 17- ethinylestradiol and 0.125 mg. of d-norgestrel are administered daily.

3. A method according to 1 wherein for the first 10–12 days 0.030 mg. of 17α-ethinylestradiol and 1 mg. of 17α-ethinyl-19-nortestosterone acetate is administered daily and for the next 11–9 days 0.050 mg. of 17α-ethinylestradiol and 2 mg. of 17α-ethinyl-19-nortestosterone acetate are administered daily.

4. A method according to claim 1 wherein for the first 10–12 days 0.030 mg. of 17α-ethinylestradiol and 1 mg. of 17α-ethinyl-19-nortestosterone acetate is administered daily and for the next 11–9 days 0.050 mg. of 17α-ethinylestradiol and 2 mg. of cyproterone acetate are administered daily.

5. A two-stage combination oral contraceptive composition comprising about 21 daily doses of a contraceptively effective combination of an estrogen a progestogen consisting essentially of, in a first stage of 10–12 successive units, a combination of:
   a. 0.030 mg. of 17α-ethinylestradiol and
      0.050 mg. of d-norgestrel,
or a combination of
   b. 0.030 mg. of 17α-ethinylestradiol and
      1 mg. of 17α-ethinyl-19-nortesterone acetate;
and, in a second stage of 11–9 successive units, a combination, when the first stage is combination (a), of
   c. 0.040 mg. of 17α-ethinylestradiol and
      0.125 mg. of d-norgestrel
or a combination, when the first state is combination (b), either of:
   d. 0.050 mg. of 17α-ethinylestradiol and
      2 mg. of 17-ethinyl-19-nortestosterone acetate; or
   e. 0.050 mg. of 17-ethinylestradiol and
      2 mg. of cyproterone acetate.

6. A contraceptive composition according to claim 5 wherein the estrogen and progestogen are in tablet form.

7. A contraceptive composition according to claim 5 wherein in the first stage, the estrogen is 0.030 mg. of 17α-ethinylestradiol and the progestogen is 0.050 mg. of d-norgestrel per unit dosage and, in the second state, 0.040 mg. of 17α-ethinylestradiol and 0.125 mg. of d-norgestrel per unit dosage.

8. A contraceptive composition according to claim 5 wherein, in the first stage, the estrogen is 0.030 mg. of 17α-ethinylestradiol and the progestogen is 1 mg. of 17α-ethinyl-19-nortestosterone acetate per unit dosage and, in the second stage, 0.050 mg. of 17α-ethinylestradiol and 2 mg. of 17α-ethinyl-19-nortestosterone acetate per unit dosage.

9. A contraceptive composition according to claim 5 containing, in the first stage 0.030 mg. of 17α-ethinylestradiol and 1 mg. of 17α-ethinyl-19-nortestosterone acetate per unit dosage and, in the second stage, 0.050 mg. of 17α-ethinylestradiol and 2 mg. of cyproterone acetate per unit dosage.

* * * * *